United States Patent [19]
Bucalo

[11] 3,938,528
[45] Feb. 17, 1976

[54] IMPLANTING AND SPLICING ARTICLES AND METHODS FOR LIVING BEINGS

[75] Inventor: Louis Bucalo, Holbrook, N.Y.

[73] Assignee: Investors in Ventures, Inc., New York, N.Y.

[22] Filed: Aug. 23, 1973

[21] Appl. No.: 390,926

Related U.S. Application Data

[63] Continuation-in-part of Ser. No. 359,429, May 11, 1973, Pat. No. 3,815,578.

[52] U.S. Cl. ............................ 128/334 C; 3/1
[51] Int. Cl.² ........................................ A61B 17/11
[58] Field of Search .... 128/1 R, 304, 334 R, 334 C, 128/335; 3/1

[56] References Cited
UNITED STATES PATENTS

| | | | |
|---|---|---|---|
| 1,983,601 | 12/1934 | Conn | 128/304 |
| 2,127,903 | 8/1938 | Bowen | 128/334 R |
| 2,514,665 | 7/1950 | Myller | 128/304 |
| 3,221,746 | 12/1965 | Noble | 128/334 R |
| 3,254,650 | 6/1966 | Collito | 128/334 C |
| 3,357,432 | 12/1967 | Sparks | 128/334 C |
| 3,435,823 | 4/1969 | Edwards | 128/334 C |
| 3,687,129 | 8/1972 | Nuwayser | 128/1 R |
| 3,700,380 | 10/1972 | Kitrilakis | 3/1 |
| 3,786,817 | 1/1974 | Palma | 128/334 R |

*Primary Examiner*—Dalton L. Truluck
*Attorney, Agent, or Firm*—Steinberg & Blake

[57] ABSTRACT

Implanting and splicing articles and methods for living beings. When an implant is introduced into the interior of a body cavity mucosa is simultaneously removed from a lining of the body cavity, and the surface from which the mucosa is removed is placed in engagement with a structure for promoting the ingrowth of tissue while being immobilized with respect to this latter structure. Thus, the leading end of an implant which first enters the cavity carries an element which removes mucosa simultaneously with the introduction of the implant and which immobilizes the surface from which mucosa has been removed, the implant carrying just to the rear of the latter element a structure for engaging the surface from which the mucosa has been removed and promoting the ingrowth of tissue. In connection with splicing, the parts to be spliced are overlapped by an elongated member having a pair of spaced sets of barbs or the like for holding together and immobilizing the spliced parts, this elongated member also carrying a structure for promoting the ingrowth of tissue, and this latter structure engages the immobilized parts. Articles of this latter type may be designed either for surrounding the parts to be spliced when the latter are either solid or tubular or for being situated in the interior of the spliced parts when the latter are tubular.

14 Claims, 6 Drawing Figures

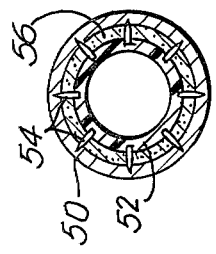
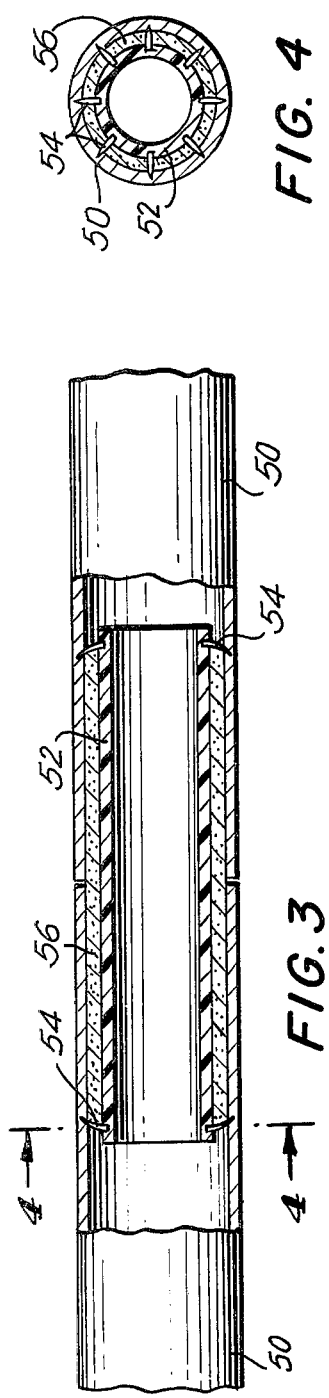
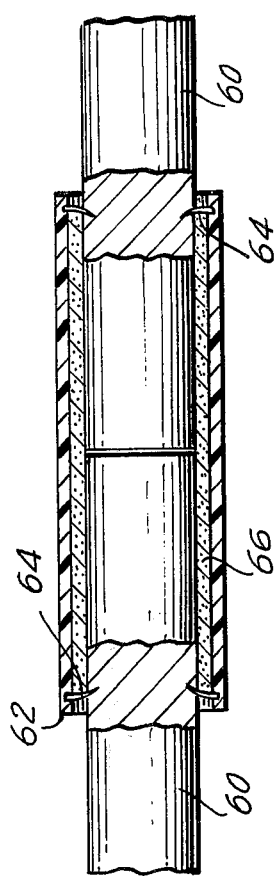
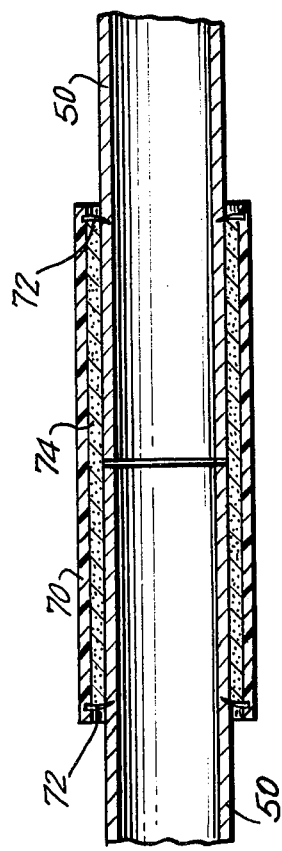

IMPLANTING AND SPLICING ARTICLES AND METHODS FOR LIVING BEINGS

CROSS REFERENCE TO RELATED APPLICATION

The present application is a continuation-in-part of copending application Ser. No. 359,429, filed May 11, 1973, now U.S. Pat. No. 3,815,578, dated June 11, 1974 and entitled Body Implants and Implanting Tool and Method.

BACKGROUND OF THE INVENTION

The present invention relates to methods and articles to be used in connection with the treatment of living beings such as human beings.

In particular, the present invention relates to implanting and splicing methods and articles.

As a result of various surgical procedures, problems are frequently encountered in connection with healing of the living tissue so that a normal stable state of the tissue is achieved as soon as possible subsequent to the surgical procedures. Thus, in connection with an implant, living tissue is required to become securely united with the implant, and up to the present time difficulties have been encountered in achieving the secure mounting of an implant in the body of a living being in a convenient and rapid manner. The same considerations apply to surgical procedures which involve uniting of body parts such as ligaments, tendons, or tubular body parts such as arteries. In connection both with implanting and splicing procedures, artificial components are introduced into the body, and the presence of these components create problems. Thus, although it is known to provide such components with structures which will encourage the ingrowth of tissue in order to achieve a secure connection between the artificial components and the living tissue, it has been found that the optimum conditions in the relationship between the living tissue and the structure for promoting the ingrowth of tissue are not present with conventional surgical procedures. Moreover, in connection with the simple splicing of tubular body parts, such as the interconnection of parts of an artery at a location where the artery has been severed, the component which is introduced to effect the splice often occupies in an undesirable manner the interior of the interconnected tubular parts, with the result that the cross section of the area through which fluid is required to flow is undesirably diminished. Conventional interconnection of separated parts of tendons, ligaments, arteries, or the like by sewing them together with suitable sutures results undesirably in the formation of scar tissue and other thickenings or bulbous growths.

SUMMARY OF THE INVENTION

It is accordingly a primary object of the present invention to provide methods and articles which will avoid the above drawbacks.

In particular, it is an object of the present invention to provide methods and articles which will greatly enhance the capability of living tissue to grow into a structure carried by a splicing element or implanted article.

It is furthermore an object of the present invention to provide methods and articles which will optimize the return of living tissue to normal stable conditions in a convenient rapid manner both with respect to the manipulations which must be performed by a surgeon as well as with respect to the healing process itself.

Thus, it is a more specific object of the present invention to provide methods and articles which will enable implants to be quickly and conveniently introduced into the body of a living being while at the same time achieving a security in the positioning of the implant in the interior of the body in a short time with minimum inconvenience on the part of the surgeon and patient.

It is moreover a further specific object of the present invention to be capable of splicing together separated parts of tendons, ligaments, arteries, or the like, with minimum inconvenience and skill on the part of the surgeon and with an assurance of return of the spliced parts to a normal condition in a minimum amount of time.

In accordance with an implanting method of the invention, when the implant is introduced into a body cavity which is lined with mucosa, the mucosa lining is removed simultaneously with the introduction of the implant and the surface from which the mucosa has been removed is immobilized and placed in engagement with a means for promoting the ingrowth of tissue. In a similar manner, when splicing together separated parts in the interior of the body, these parts are overlapped by an elongated member which carries a pair of spaced immobilizing means for immobilizing the overlapped parts so that they remain held together, and wherever it is considered desirable between the pair of immobilizing means the splicing member carries a structure for promoting the ingrowth of tissue to engage the spliced parts so that a secure connection between them is achieved.

BRIEF DESCRIPTION OF DRAWINGS

The invention is illustrated by way of example in the accompanying drawings which form part of this application and in which:

FIG. 3 is a fragmentary schematic partly sectional illustration of a splicing method and article according to the invention;

FIG. 4 is a transverse section of the features illustrated in FIG. 3 taken along line 4—4 of FIG. 3 in the direction of the arrows;

FIG. 5 is a partly sectional fragmentary schematic illustration of a further embodiment of a splicing method and article according to the invention; and FIG. 6 is a partly sectional fragmentary schematic illustration of yet another embodiment of a splicing method and article of the present invention.

DESCRIPTION OF PREFERRED EMBODIMENTS

Figure 1:
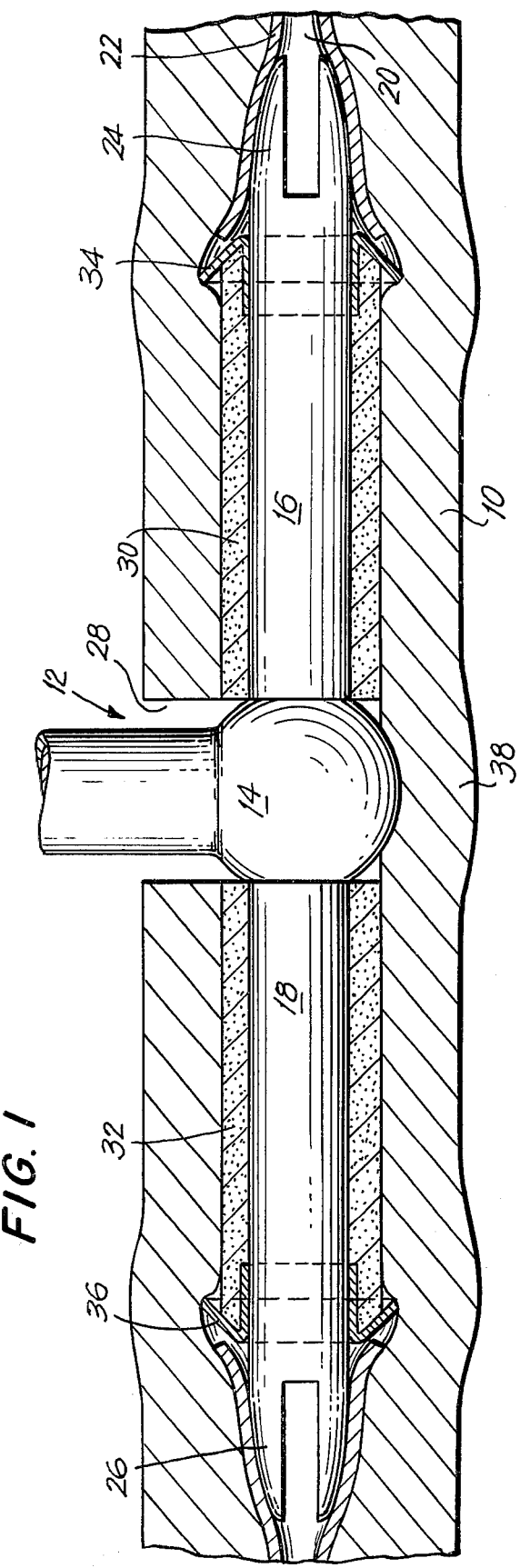
FIG. 1 is a schematic illustration of an implanting method and article according to the invention.

The invention is illustrated by way of example in FIG. 1 in connection with an implant in the form of a valve capable of reversibly interrupting the flow of spermcarrying fluid through a vas deferens 10 which is schematically illustrated. However, it is to be understood that the invention is applicable to other implants, as will be apparent from the description which follows. Thus, it will be seen that in the illustrated example the implant 12 is in the form of a valve which has a central region 14 and a pair of elongated portions 16 and 18 extending in opposite directions from the central region 14.

These elongated portions 16 and 18 are of a hollow tubular construction, and the flow therethrough can be controlled by turning an internal bored valve member which turns in a known way within the central region 14 of the implant 12.

The illustrated vas deferens 10 has an interior lumen 20 lined with mucosa 22. The elongated portions 16 and 18 of the implant 12 terminate in slotted free end regions 24 and 26, the illustrated slots being provided to prevent blocking of the hollow interiors of the tubular portions 16 and 18. Prior to introduction of the implant 12, the vas 10 is surgically cut transversely only up to the lumen 20 so that in this way the vas 10 is provided with a notch 28 through which access is had to the lumen 20. The tubular portions 16 and 18 are introduced into the lumen one after the other so that the end portions 24 and 26 may be considered as the leading ends of the implant inasmuch as these are the ends which first enter into the interior cavity 20 which is lined with the mucosa 22 as pointed out above.

The elongated portions 16 and 18 of the implant 12 respectively carry means 30 and 32 for promoting the ingrowth of tissue. Each of the means 30 and 32 may take the form of a structure which has a large number of relatively small spaces into which tissue readily grows. For example, the means 30 and 32 may be formed by fine gold or platinum wire wound around the portions 16 and 18 and forming a plurality of tiny interstices which form the spaces into which the tissue readily grows. In the illustrated example, however, the pair of means 30 and 32 each is in the form of a matrix having pores which form the spaces into which the tissue readily grows. Such a matrix may be formed by vapor-deposition of metal in a suitable evacuated atmosphere. For example gold may be sputtered onto the exterior surfaces of the portions 16 and 18 to form the porous matrixes 30 and 32 which will act to promote the ingrowth of tissue.

It has been found that if the mucosa lining 22 is in engagement with the means 30 and 32 for promoting ingrowth of tissue, the tissue will not readily and rapidly grow into the ingrowth means. Therefore, in accordance with the invention the layer of mucosa 22 is removed, and in the illustrated example the removal of the mucosa lining 22 takes place simultaneously with the introduction of the implant into the body cavity. For this purpose the elongated portions 16 and 18 respectively carry a pair of mucosa-removal means 34 and 36. Each of the means 34 and 36 is in the form of a simple ring of a suitable metal, for example, having an inner cylindrical portion directly surrounding the tubular parts 16 or 18 and an outer inclined portion providing each of the means 34 and 36 with the illustrated V-shaped cross section. Thus, the outer part of each of the means 34 and 36 tapers outwardly and rearwardly with respect to the direction of insertion of the implant. Moreover it will be noted that the pair of ingrowth means 30 and 32 extend from the central region 14 of the implant 12 all the way up to the mucosa-removal means 34 and 36, respectively.

When the above-described implant 12 is introduced through the cutout 28 into the interior cavity 20, the leading end 24 or 26 is immediately followed by the mucosa removing means 34 or 36 which acts automatically to engage at its outer periphery the inner surface of the cavity, removing the mucosa layer 22 as the leading end 24 or 26 advances along the interior of the cavity 20. Thus the outer periphery of the means 34 or 36 is relatively thin and sharp and easily scrapes away the mucosa layer 22 so that the latter is pushed away from the inner surface of the organ 10 in advance of the mucosa removal means. The surface from which the mucosa has been automatically removed in this way simultaneously with the introduction of the implant immediately comes into engagement with the exterior surface of the ingrowth means 30 or 32, so that there is no layer of mucosa to inhibit the ingrowth of tissue.

In the example illustrated in FIG. 1 the notch or cutout 28 extends only up to the lumen 20, so that part of the organ 10 remains uncut and uninterrupted along the region 38. Such an arrangement is of particular advantage since nerves which extend through the portion 38 will not be cut. However, such a procedure is also of advantage because the uncut and thus uninterrupted portion 38 serves to hold the organ 10 together preventing the surfaces from which the mucosa has been removed from moving with respect to the ingrowth means 30 and 32. The pressure of the outer edges of the mucosa removal means 34 and 36 against the inner surface of the organ 10 also serves to contribute to the immobilizing of the surfaces which engage the ingrowth means 30 and 32. Thus, with the tissue which engages the ingrowth means 30 and 32 immobilized and with the mucosa layer removed from this surface, an extremely rapid and profuse ingrowth of tissue takes place into the spaces of the pair of means 30 and 32, achieving in this way an extremely secure connection.

Figure 2:
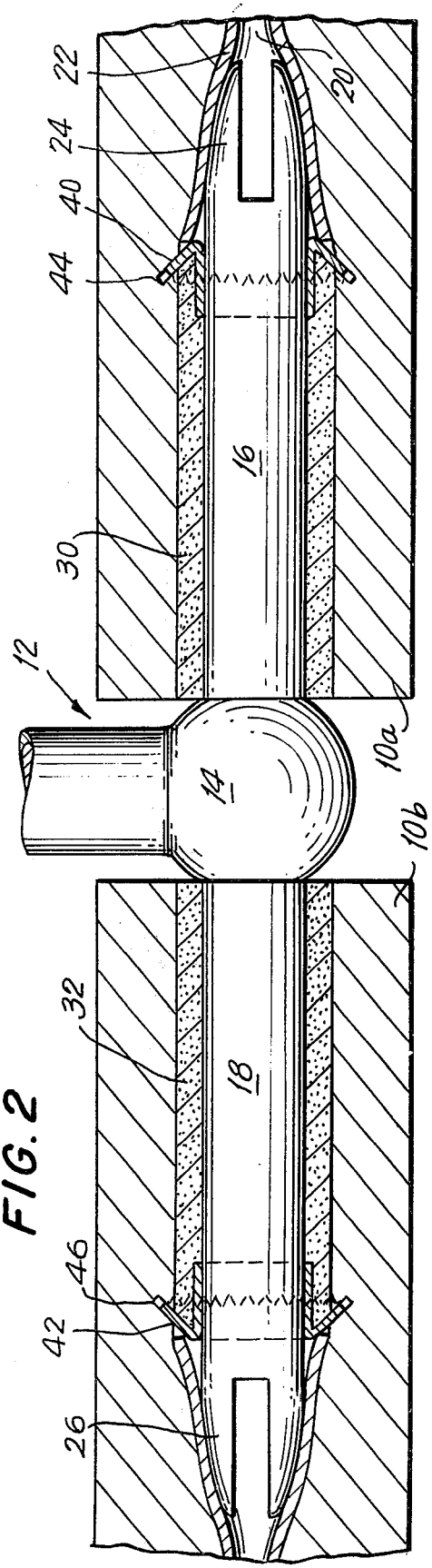
FIG. 2 is a schematic illustration of a further embodiment of an implanting method and article according to the invention.

The embodiment of the invention which is illustrated in FIG. 2 is very similar to that of FIG. 1. Thus, the valve or implant 12 is of the same construction as the implant of FIG. 1. Also, the pair of means 30 and 32 for promoting the ingrowth of tissue are identical with the means 30 and 32 of FIG. 1. However, FIG. 2 illustrates a surgical procedure where the vas is completely cut through so as to have a pair of portions 10a and 10b, and the elongated portions 16 and 18 of the implant 12 are separately introduced into these organ portions 10a and 10b.

The pair of mucosa-removing means 40 and 42 of FIG. 2 differ from the mucosa-removing means 34 and 36 of FIG. 1 in that the pair of means 40 and 42 have jagged outer peripheral edges 44 and 46 provided with relatively sharp pointed teeth. With this construction when the elongated portions 16 and 18 are introduced into the cavity 20, the pair of mucosa removal means 40 and 42 will act in the manner described above to automatically remove the mucosa lining 22 as the leading ends 24 and 26 continue to advance along the interior cavity 20. However, with this construction since the portions 10a and 10b are no longer held together by the uninterrupted part 38 shown in FIG. 1, the irregular edges 44 and 46 dig at their pointed regions into the tissue which forms the portions 10a and 10b and prevent them from being pulled apart from each other. The result is that with this construction also not only will the mucosa layer 22 be automatically removed simultaneously with the insertion of the implant, and the surface from which the mucosa has been removed will automatically engage the means 30 and 32 for promoting the ingrowth of tissue, but in addition the outer jagged edge regions 44 and 46 form a pair of immobilizing means for immobilizing the surfaces from which the mucosa layer 22 has been removed so that these surfaces do not move with respect to the ingrowth means 30 and 32. As a result of this immobilizing of the surfaces from which the mucosa layer has been removed, the embodiment of FIG. 2 also achieves an extremely rapid and highly profuse ingrowth of tissue into the tiny spaces within the pair of means 30 and 32 so as to provide an extremely secure connection in this way.

It is furthermore to be noted that in the particular example of FIGS. 1 and 2 where the implant is in the form of a vas valve for reversibly interrupting the flow of fluid which carries sperm, the union of the tissue with the implant at the ingrowth means provides a highly effective seal at the exterior of the implant preventing any sperm from travelling along the exterior of the implant, so that the purpose of the implant cannot be defeated by sperm which bypass the implant.

As has been indicated above, the principles of the invention described above in connection with FIGS. 1 and 2 are generally applicable to all types of surgical procedures. Thus, the principles of the invention are illustrated in FIGS. 3-6 in connection with an implant which has the form of a tubular splicing element. Referring to FIG. 3, there are schematically illustrated therein a pair of tubular parts 50 in the interior of a living being. For example these parts 50 may form parts of an artery which has been cut through either accidentally or surgically, and FIG. 3 illustrates a method and article of the invention for interconnecting the parts 50. Thus, referring to FIG. 3 it will be seen that the article of the invention illustrated therein includes an elongated tubular member 52 made of any suitable metal or plastic which is compatible with the body and having at the region of its opposed ends, respectively, a pair of immobilizing means 54 each of which is in the form of a series of sharply pointed barbs distributed around the tubular member 52 in the manner shown most clearly in FIG. 4. This member 52 may be made of a suitable plastic in which the inner ends of the barbs 54 are embedded, for example. It will be noted that the pointed free ends of the barbs 54 curve inwardly toward the central region of the tubular member 52. In accordance with a further feature of the invention, the tubular member 52 carries at its exterior surface between the pair of immobilizing means 54 a means 56 for promoting the ingrowth of tissue, and this means 56 may have the construction of either of the means 30 or 32 described above.

According to the method of the invention which is illustrated in FIGS. 3 and 4, the opposed end regions of the member 52 are introduced into the hollow interiors of the parts 50, and the pointed outer ends of the barbs 54 dig into the tissue which forms the tubular members 50 so as to prevent the latter from being pulled apart from each other. At the same time, the inner surfaces of the parts 50 which are overlapped by the tubular member 52 and which are situated between the pair of means 54, come into engagement with the exterior surface of the means 56 for promoting the ingrowth of tissue, so that in this case also the tissue which forms the parts 50 grows rapidly and profusely into the tiny spaces of the means 56 to provide an exceedingly secure connection with the embodiment of FIGS. 3 and 4. It is to be noted that the free ends of the parts 50 may be located close enough to each other so that they will grow into each other, thus providing further security in the connection.

In the event that the nature of the parts 50 is such that the interior surfaces thereof are lined with mucosa, then of course the barbs 54 may be replaced with the elements 40 and 42 which serve to automatically remove the mucosa lining as well as to immobilize the tissue which engages the means 56, so as to enhance the ingrowth of tissue in the manner described above.

Of course, with the arrangement shown in FIGS. 3 and 4, the thickness of the parts 52 and 56 is exaggerated for the sake of clarity, and the hollow interior of the interconnected parts 50 is diminished in cross section only to a small extent with the article of the invention. However, it is possible to further reduce any disadvantage from diminishing the cross section of the interior of the interconnected parts 50 by making the element 52 as well as the barbs 54 of a material which disintegrates and disappears after elapse of a given period of time. Such materials are well known in the case of dissolving sutures, for example.

It is furthermore to be understood that the invention is not necessarily limited to implanting and splicing articles and methods where the implant or splicing article are introduced into the interior of a body cavity. Thus, FIG. 5 shows how the invention may be used in connection with the splicing of ligament or tendon parts 60. In this case the article of the invention includes an elongated tubular member 62 having opposed open ends through which the parts 60 are introduced into the interior of the tubular member 62, and these parts 60 may be introduced to such an extent that their ends are substantially in abutting relation and will grow together. The tubular member 62 thus is placed in overlapping relation with respect to the free end regions of the parts 60 which are to be spliced together.

In the example of FIG. 5 the tubular member 62 is provided at its interior with a pair of immobilizing means in the form of sets of barbs 64 which are also pointed inwardly although they are situated at the interior of the tubular member 62 as illustrated. The barbs 64 may be embedded at their outer ends in the material which forms the tubular member 62. In this case also between the pair of immobilizing means 64 the inner surface of the tubular member 62 carries a means 66 for promoting the ingrowth of tissue, this means 66 having the construction of the means 56, 30, or 32, for example.

Thus, with the embodiment of FIG. 5 the tendon or ligament parts 60 are simply introduced through the opposed open ends of the tubular member 62 into the interior thereof, and the pair of immobilizing means 64 will act to prevent the parts 60 from moving out of the tubular member 62. At the same time the exterior surface of the parts 60 which are in the interior of the tubular member 62 comes into engagement with the means 66 for promoting the ingrowth of tissue, and because the surfaces which engage the means 66 are immobilized a rapid profuse ingrowth of tissue is assured. Thus the immobilizing means 64 serves in the same way as the means 54 of FIG. 3 not only to prevent the interconnected parts from moving apart from each other but also for immobilizing the surfaces which engage the means for promoting the ingrowth of tissue so as to enhance the rapidity and profusion of the ingrowth of tissue. Naturally if the nature of the parts 60 is such that there is a layer of mucosa which normally would be situated in engagement with the tissue ingrowth means 66, the pair of means 64 may be replaced by the pair of means 40 and 42 of FIG. 2 which are provided at their outer edge regions with the immobilizing parts while at the same time being capable of automatically removing the layer of mucosa which thus is prevented from entering into the interior of the tubular member 62 beyond the immobilizing means, thus assuring that the surface of the tissue which engages the means for promoting the ingrowth of tissue is free of mucosa.

It is to be noted that the features illustrated in FIG. 5 are not limited to solid parts such as tendons or ligaments. Thus, FIG. 6 shows how the features of FIG. 5 may be utilized in connection with interconnecting a pair of parts 50 of the type shown in FIG. 3. Thus, FIG. 6 shows an outer tubular member 70 which may be identical with the member 62 except for its size, this member 70 carrying in the region of its opposed ends and in its interior the rings of barbs 72 which form the pair of immobilizing means, and in the illustrated example between the pair of immobilizing means 72 the inner surface of the tubular member 70 carries a means 74 for promoting the ingrowth of tissue and having the construction of any of the above-described means for promoting the ingrowth of tissue. Thus, in this case the pair of tubular parts 50 will be introduced into the interior of the tubular member 70 through the opposed open ends thereof, and the extent of introduction of the parts 50 may be such that the free ends substantially abut against each other so that they will grow together. The barbs 72 dig into the tissue which forms the parts 50 so as to prevent the latter from being withdrawn from the tubular member 70, and at the same time the portions which engage the means 74 are immobilized so as to be incapable of moving with respect to the tissue ingrowth means 74. In this way a rapid profuse ingrowth of tissue is assured. In this case also if the nature of the parts 50 is such that there is a layer of mucosa which would otherwise become located between the tissue and the means 74, the pair of immobilizing means 72 could be constructed in a manner similar to the pair of means 40 and 42 so that they would function to remove the mucosa layer simultaneously with the introduction of the parts 50 while at the same time immobilizing the portions of the parts 50 which engage the means 74. Of course, when the parts 40 and 42 replace the parts 64 or 72, the tapering or flaring region extends inwardly from the circular part which engages in this case the inner surface of the tubular member 62 or 70, and of course the inclination of the tapered part is such that it is inclined inwardly toward the interior of the tubular member 62 or 70 with the pointed or jagged free edge which functions as the immobilizing means being situated at the innermost edge of the means which functions both as the mucosa removal means and the immobilizing means.

Of course, the advantage of the arrangement shown in FIG. 6 as compared to that of FIG. 3 is that the interior of the parts 50 is not diminished in any way and these parts 50 communicate directly with each other so that there is no interruption or any diminishing of the cross section of the hollow interiors of the parts 50 so that an exceedingly effective splice can be achieved with the features of the invention which are illustrated in FIG. 6. Also, in the case of FIGS. 5 and 6 it is possible to construct the tubular members and the immobilizing means of materials similar to the known suturing material which dissolves away after a given period of time. This latter period of time is of course sufficiently long to permit the tissue ingrowth to take place to an extent sufficient to achieve the required secure connection.

While with the embodiments of FIGS. 5 and 6 there is an illustration of a means for promoting ingrowth of tissue, in some cases the nature of the tissue which forms the parts 50 and 60 is such that this tissue will very rapidly grow together at the abutting free ends of the parts which are to be spliced together. Thus, where this latter condition prevails it is possible to omit the means for promoting the ingrowth of tissue, and in this case the structure and method of the invention would involve only an outer tubular member having at its interior in the region of its opposed ends the pair of immobilizing means for immobilizing the parts which are overlapped by the tubular member so that the free ends of the parts 50 or the parts 60 can readily grow together to provide an exceedingly secure connection even without an ingrowth means.

It is thus apparent that a number of exceedingly great advantages are achieved with the features of the invention described above. It will be seen that the manipulations which a surgeon must perform are minimal and require minimal skill, so that an exceedingly great convenience and saving of time is achieved for the surgical procedure itself. In addition, the time which otherwise would be involved in removing a layer of mucosa is saved because of the automatic removal of the layer of mucosa simultaneously with the introduction of the implant or overlapping of the splicing element with the parts which are to be spliced together. Furthermore, an exceedingly secure connection is assured in all cases with minimizing of disadvantages such as those which would result from a reduction in the cross section of the interior of a tube along which a body fluid is required to flow. It is furthermore emphasized that the outstanding results which are achieved with the invention flow not only from the removal of the mucosa layer at a surface which engages a means for promoting the ingrowth of tissue but also from the immobilizing of this surface so that it does not move with respect to the means for promoting the ingrowth of tissue.

What is claimed is:

1. In an implanting method, the steps of introducing an implant into a body cavity which is lined with mucosa while simultaneously removing mucosa from at least part of the cavity and placing in engagement with an inner surface of the cavity from which the mucosa has been removed a means carried by the implant for promoting the ingrowth of tissue.

2. In a method as recited in claim 1 and wherein the means for promoting the ingrowth of tissue is placed in engagement with the inner surface of the cavity simultaneously with the removal of mucosa therefrom.

3. In a method as recited in claim 1 and including the step of immobilizing the inner surface of the cavity which is placed in engagement with the means for promoting the ingrowth of tissue.

4. In a method as recited in claim 1 and wherein the means for promoting the ingrowth of tissue is placed in engagement with the inner surface of the cavity simultaneously with the removal of mucosa therefrom, and including the step of immoblizing the inner surface of the cavity which is placed in engagement with the means for promoting the ingrowth of tissue.

5. In a method as recited in claim 1 and wherein the implant is a valve and the cavity is the lumen of a vas deferens.

6. In a method as recited in claim 5 and wherein the valve has a central region and a pair of elongated portions extending in opposite directions from said central region, the mucosa being removed along the lumen of the vas deferens from the central region of the valve up to locations adjacent free ends of the elongated portions of the valve, and said elongated portions of the valve carrying the means for promoting the ingrowth of tissue which engages the inner surface of the vas deferens from which mucosa has been removed simultaneously with introduction of the elongated portions of the valve into the lumen of the vas deferens.

7. In a method for interconnecting a pair of adjoining internal body parts in the interior of a living being, the steps of placing an elongated member in overlapping relationship with respect to the pair of adjoining parts, immobilizing those portions of the adjoining parts which overlap said member so that the adjoining parts are held together by said elongated member and are maintained stationary with respect thereto, and placing between the elongated member and the immobilized portions of said parts which remain stationary with respect to said elongated member a means for promoting the ingrowth of tissue into tight intimate contact with a surface of said elongated member, said adjoining parts being hollow and said member being of a tubular configuration and inserted into the interior of said hollow parts, and removing mucosa from the interior of said adjoining parts at the portions thereof which are immobilized prior to placing said portions in engagement with said means for promoting the ingrowth of tissue.

8. In a method for interconnecting a pair of adjoining internal body parts in the interior of a living being, the steps of introducing the adjoining parts into the interior of an elongated tubular member which has opposed open ends by inserting the adjoining parts into the interior of the tubular member respectively through the opposed open ends thereof until said parts are substantially adjacent each other so that the tubular member overlaps portions of said parts which are situated in the interior of said tubular member, immobilizing the portions of the parts which are situated in the interior of the tubular member by way of means carried by the tubular member so as to maintain the portions in the interior of the tubular member stationary with respect thereto, and placing in engagement with the immobilized portions of said parts which remain stationary with respect to said tubular member a means for promoting the ingrowth of tissue into tight intimate contact with an inner surface of said tubular member.

9. In a method as recited in claim 8 and including the step of inserting said parts respectively through said open ends into said tubular member until free ends of said parts are substantially in abutting relationship with respect to each other.

10. In a method as recited in claim 9 and wherein said parts are solid.

11. In a method as recited in claim 9 and wherein said parts are hollow.

12. In an implant which is to be introduced into the interior of a living being, an elongated portion having an exterior surface extending between its ends and terminating in a leading end which first enters into the interior of a body cavity when the implant is introduced, said elongated portion carrying at the region of said leading end thereof a means for removing a layer of mucosa simultaneously with the movement of said elongated portion into the cavity, and means for promoting the ingrowth of tissue carried by said elongated portion at said exterior surface thereof and extending from said mucosa removing means away from said leading end so that the surface of the body cavity from which mucosa has been removed engages said means for promoting the ingrowth of tissue.

13. The combination of claim 12 and wherein said means for removing mucosa has an irregular free edge for digging into a wall which defines part of the cavity for immobilizing that part of the wall which engages the means for promoting the ingrowth of tissue.

14. The combination of claim 13 and wherein said elongated portion forms part of a valve which is to be introduced into the lumen of a vas deferens.

* * * * *